United States Patent [19]

Rheinheimer et al.

[11] Patent Number: 5,085,685
[45] Date of Patent: Feb. 4, 1992

[54] CARBOXYLIC ACID DERIVATIVES

[75] Inventors: Joachim Rheinheimer, Ludwigshafen; Karl Eicken, Wachenheim; Uwe J. Vogelbacher, Ludwigshafen; Wolfgang Rohr, Wachenheim; Thomas Kuekenhoehner, Frankenthal; Karl O. Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 566,536

[22] Filed: Aug. 13, 1990

[30] Foreign Application Priority Data

Aug. 19, 1989 [DE] Fed. Rep. of Germany ....... 3927382

[51] Int. Cl.$^5$ ............... C07D 239/32; C07D 239/46; C07D 401/12; A01N 43/54
[52] U.S. Cl. ........................................... 71/92; 71/77; 544/300; 544/301; 544/302; 544/310; 544/311; 544/312; 544/313; 544/314; 544/316; 544/318; 544/319
[58] Field of Search ............... 71/92, 77; 544/300, 544/301, 302, 312, 316

[56] References Cited

FOREIGN PATENT DOCUMENTS

| | | |
|---|---|---|
| 0223406 | 5/1987 | European Pat. Off. . |
| 0249707 | 12/1987 | European Pat. Off. . |
| 0249708 | 12/1987 | European Pat. Off. . |
| 0287072 | 10/1988 | European Pat. Off. . |
| 0287079 | 10/1988 | European Pat. Off. . |
| 0346789 | 12/1989 | European Pat. Off. . |

*Primary Examiner*—John M. Ford

*Attorney, Agent, or Firm*—Keil & Weinkauf

[57] ABSTRACT

Carboxylic acid derivatives of the general formula I

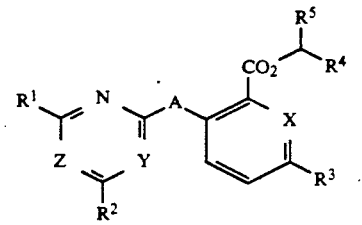

where
$R^1$ and $R^2$ are each $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
$R^3$ is hydrogen, hydroxyl, cyano, nitro, formyl, halogen, unsubstituted or substituted amino, $C_1$–$C_4$-alkyl, $C_1$–$C_4$-alkoxy, $C_3$–$C_6$-alkenyl, $C_3$–$C_6$-alkenyloxy, $C_3$–$C_6$-alkynyl or $C_3$–$C_6$-alkynyloxy;
$R^4$ is hydrogen or $C_1$–$C_4$-alkyl;
$R^5$ is unsubstituted or substituted five-membered hetaryl or isoxazolinyl or —$CR^6$=$NOR^7$;
$R^6$ is hydrogen or unsubstituted or substituted $C_1$–$C_4$-alkyl, $C_3$–$C_8$-cycloalkyl or phenyl;
$R^7$ is unsubstituted or substituted $C_1$–$C_4$-alkyl, $C_3$–$C_6$-alkenyl, $C_3$–$C_8$-cycloalkyl or phenyl;
A is oxygen or sulfur;
X is nitrogen or methine =$CR^8$—;
$R^8$ is one of the radicals $R^3$, or $R^8$ and $R^3$ together form unsubstituted or substituted 1,3-butadiene-1,4-yl or aza-1,3-butadiene-1,4-yl, and
Y and Z are each nitrogen or methine =CH—, their preparation and agents containing them.

7 Claims, No Drawings

CARBOXYLIC ACID DERIVATIVES

The present invention relates to carboxylic acid of the general formula I

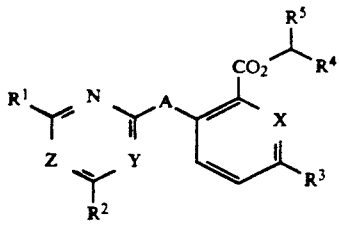

where

R$^1$ and R$^2$ are each C$_1$-C$_4$-alkyl, C$_1$-C$_4$-haloalkyl, C$_1$-C$_4$-alkoxy, C$_1$-C$_4$-haloalkoxy or C$_1$-C$_4$-alkylthio;

R$^3$ is hydrogen, hydroxyl, cyano, nitro, amino, formyl, halogen;

C$_1$-C$_4$-alkyl, C$_1$-C$_4$-alkoxy, C$_3$-C$_6$-alkenyloxy, C$_3$-C$_6$-alkynyl or C$_3$-C$_6$-alkynyloxy, where these groups may carry from one to five halogen atoms and/or a C$_1$-C$_4$-alkoxy or C$_1$-C$_4$-alkylthio group;

C$_1$-C$_4$-alkylamino, di-C$_1$-C$_4$-alkylamino, phenylamino, N-phenyl-N-C$_1$-C$_4$-alkylamino or C$_1$-C$_6$-alkylcarbonylamino;

R$^4$ is hydrogen or C$_1$-C$_4$-alkyl;

R$^5$ a five-membered hetaryl radical which contains one or two nitrogen atoms and an oxygen or sulfur atom, or is an isoxazolinyl radical, where these ring systems may carry from one to four halogen atoms and/or one or two of the following radicals: C$_1$-C$_6$-alkyl, C$_1$- or C$_2$-haloalkyl, C$_1$-C$_4$-alkoxy, C$_1$- or C$_2$-haloalkoxy, C$_3$-C$_8$-cycloalkyl, phenyl or pyridyl, where the aromatic radicals in turn may carry from one to five halogen atoms and/or from one to three of the radicals stated for R$^1$;

or a group —CR$^6$=NOR$^7$, where

R$^6$ is hydrogen;

C$_1$-C$_4$-alkyl which may carry from one to five halogen atoms and/or one of the following radicals: C$_1$-C$_4$-alkoxy, C$_1$-C$_4$-alkylthio or phenyl, where the phenyl radical in turn may carry from one to five halogen atoms and/or from one to three of the radicals stated for R$^1$, or R$^6$ is C$_3$-C$_8$-cycloalkyl which may carry from one to three C$_1$-C$_4$-alkyl groups, or R$^6$ is phenyl which may carry from one to five halogen atoms and/or from one to three of the radicals stated for R$^1$, and R$^7$ is C$_1$-C$_8$-alkyl or C$_3$-C$_6$-alkenyl which may carry from one to five halogen atoms and/or one of the following radicals: C$_1$-C$_4$-alkoxy, C$_1$-C$_4$-alkylthio or phenyl, where the phenyl radical in turn may carry from one to five halogen atoms and/or from one to three of the radicals stated for R$^1$;

C$_3$-C$_8$-cycloalkyl which may carry from one to three C$_1$-C$_4$-alkyl groups;

phenyl which may carry from one to five halogen atoms and/or from one to tnree of the radicals stated for R$^1$;

A is oxygen or sulfur;

X is nitrogen or a methine group =CR$^8$—, where R$^8$ is one of the radicals R$^3$, or R$^8$ and R$^3$ together form a 1,3-butadiene-1,4-diyl or aza-1,3-butadiene-1,4-diyl chain, where these chains in turn may carry from one to four halogen atoms and/or one or two of the radicals stated for R$^1$;

Y and Z are each nitrogen or a methine group =CH—, and salts thereof which can be used in agriculture.

The present invention furthermore relates to processes for the preparation of the compounds I and their use as herbicides and growth regulators.

The literature (EP-A 223 406, EP-A 249 708, EP-A 287 072 and EP-A 287 079) describes herbicidal salicylic acid derivatives and their sulfur analogs.

It is an object of the present invention to provide compounds which have herbicidal and growth-regulating properties which are improved with regard to tolerance by crops and application rate.

We have found that this object is achieved by the carboxylic acid derivatives I defined at the outset.

We have also found processes for the preparation of the compounds, methods for controlling undesirable plant growth and methods for influencing plant growth with the compounds I and the corresponding agents.

The carboxylic acid derivatives of the formula I are obtainable by various methods. For example, they are particularly advantageously obtained by reacting a corresponding aromatic ortho-hydroxy- or ortho-mercaptocarboxylic acid of the formula II with a heterocycle of the formula III in a conventional manner in the presence of a base.

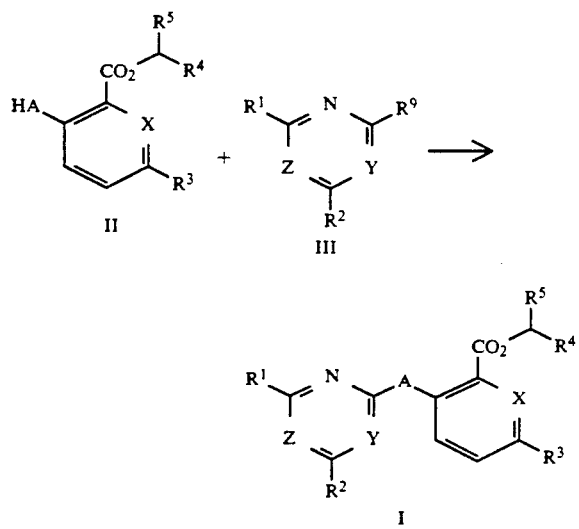

In formula III, Rs is a leaving group, such as halogen, eg. fluorine, chlorine, bromine or iodine, or aryl- or alkylsulfonyl, such as toluenesulfonyl, methylsulfonyl or trifluoromethylsulfonyl.

Suitable bases are alkali metal or alkaline earth metal hydrides, hydroxides, carbonates, bicarbonates and amides, as well as alkyl- or arylalkali metal compounds, alkali metal and alkaline earth metal alcoholates and tertiary amines.

In particular, sodium hydride, calcium hydride, sodium hydroxide, potassium hydroxide, sodium carbonate, potassium carbonate, sodium bicarbonate, potassium bicarbonate, sodium methylate, potassium tert-butylate and sodium amide are used as bases in this reaction.

When inorganic bases are used, it may be advantageous for the reaction rate to add a phase transfer catalyst, such as a crown ether or an organic ammonium salt, to the reaction mixture.

The heterocycles III required for the reaction are known or are obtainable in a known manner.

The compounds I can also be obtained by first converting a carboxylic acid IV into the halide or another activated form of the carboxylic acid in a conventional manner and then esterifying these derivatives with an alcohol of the formula V.

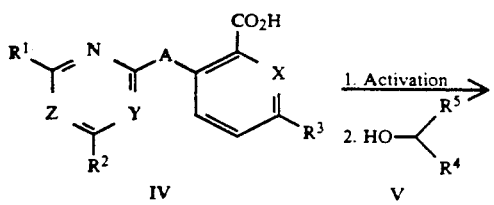

IV     V

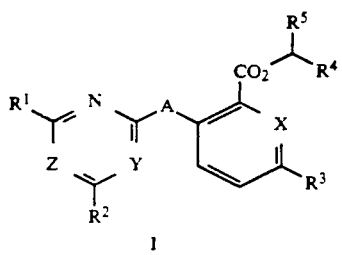

I

In addition to halides, such as chloride, bromide or iodide, other activated forms of the carboxylic acid are imidazolides.

The carboxylic acids IV required for the esterification are known. The alcohols of the formula V can be prepared by known methods.

With regard to the herbicidal activity, preferred compounds I are those in which the substituents have the following meanings:

$R^1$ and $R^2$ are each alkyl, such as methyl, ethyl, propyl, 1-methylethyl, butyl, 1-methylpropyl, 2-methylpropyl or 1,1-dimethylethyl, preferably methyl, ethyl or 1-methylethyl;

haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluo 2,2-dichloro-2-fluoroethyl, 2,2,2-trichloroethyl or pentafluoroethyl, in particular difluoromethyl, trifluoromethyl, 2,2,2-trifluoroethyl or pentafluoroethyl, preferably difluoromethyl or trifluoromethyl;

alkoxy, in particular methoxy, ethoxy, propoxy, 1-methylethoxy, butoxy, 1-methylpropoxy, 2-methylpropoxy or 1,1-dimethylethoxy, preferably methoxy or ethoxy;

haloalkoxy, such as difluoromethoxy, trifluoromethoxy, chlorodifluoromethoxy, dichlorofluoromethoxy, 1-fluoroethoxy 2-fluoroethoxy, 2,2-difluoroethoxy, 1,1,2,2-tetrafluoroethoxy, 2,2-trifluoroethoxy, 2-chloro-1,1,2-trifluoroethoxy or pentafluoroethoxy, preferably difluoroethoxy or trifluoromethoxy, and/or alkylthio, such as methylthio, ethylthio, propylthio, 1-methylethylthio, butylthio, 1-methylpropylthio, 2-methylpropylthio or 1,1-dimethylethylthio, preferably methylthio or ethylthio;

$R^3$ is hydrogen, hydroxyl, cyano, nitro, amino, formyl; halogen, such as fluorine, chlorine, bromine or iodine, preferably fluorine or chlorine;

alkyl as stated in general and in particular for $R^1$; alkoxy as stated for $R^1$, preferably methoxy, alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-metmethyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-metmethyl-4-pentenyl, 2-methyl-4-pentenyl, 3-methyl-4-pentenyl, 4-1,1-dimethyl-3-butenyl, 1,2-dimethyl-2-butenyl, 1,2-dimethyl-3-butenyl1,1,3-dimethyl-2-butenyl, 1,3-dimethyl-3-butenyl, 2,2-dimethyl-3-butenyl, butenyl, 2,3-dimethyl-3-butenyl, 1-ethyl-2-butenyl, 1-ethyl-3-butenyl, 1,1,2-trimethyl-2-propenyl, 1-ethyl-1-methyl-2-propenyl or 1-ethyl-2-methyl-2-propenyl, in particular 2-propenyl, 2-butenyl, 3-methyl-2-butenyl or 3-methyl-2-pentenyl, preferably 2-propenyl or 2-butenyl;

alkenyloxy, such as prop-2-enyloxy, but-2-enyloxy, but-3-enyloxy, 1-methyl-prop-2-enyloxy, 2-methylprop-2-enyloxy, 2-methylprop-2-enyloxy, pent-2-enyloxy, pent-3-enyloxy, pent-4-enyloxy, 1-methylbut-2-enyloxy, 2-methylbut-2-enyloxy, 3-methylbut2-1-methylbut-3-enyloxy,2-methyl but-3-enyloxy, 1,1-dimethylprop-2-enyloxy, 1,2-dimethylprop-2-enyloxy, 1-ethylprop-2-enyloxy, hex-2-enyloxy, hex-3-enyloxy, hex-4-enyloxy, hex-5-enyloxy, 1-methylpent-2-enyloxy, 2-methylpent-2-enyloxy, 3-4-methylpent-2-enyloxy, 1-methy 2-methylpent-3-enyloxy,3-methylpent-3-enyloxy, 4-methyl-pent-3-enyloxy, 1-methylpent-4-enyloxy, enyloxy, 3-methylpent-4-enyloxy, 4-methylpent-4-enyloxy, 1,1-dimethylbut-2-enyloxy, 1,2-dimethylbut-2-enyloxy, 1,3-dimethylbut-2-enyloxy, 2,3-dimethylbut-2-enyl, 1,1-dimethylbut-3-enyloxy, 1,2-dimethylbut-3-dimethylbut-3-enyloxy, 2,3-dimethylbut-3-enyloxy, 2,2-dimethylbut-3-enyloxy, 1-ethylbut-2-enyloxy, 2-ethyl-but2-enyloxy, 1-ethylbut-3-enyloxy, 1,1,2-trimethylprop-2-enyloxy, 1-ethyl-1-methylprop-2-enyloxy or 1-ethylen-2-methylprop-2-enylo2-propenyloxy or 2-butenyloxy;

alkynyl, such as 2-propynyl, 2-butynyl, 3-butynyl, 1-methyl-2-propynyl, 2-pentynyl, 3-pentynyl, 1-methyl-2-butynyl,1-methyl-3-butyny1,2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-metmethyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, butynyl or 1-ethyl-1-methyl-2-propynyl, preferably 2-propynyl or 2-butynyl;

alkynyloxy, such as prop-2-ynyloxy, but-2-ynyloxy, but3-ynyloxy, 1-methylprop-2-ynyloxy, pent-2-ynyloxy 3-ynyloxy, pent-4-ynyloxy, 1-methylbut-2-ynyloxy, 1-methylbut-3-ynyloxy,2-methylbut-3-ynyloxy,1,1-dimethylprop-2-ynyloxy, 1-ethylprop-2-ynyloxy, hex-3-ynyloxy, hex-4-ynyloxy, hex-5-ynyloxy, 1-methylpent-2-ynyloxy, 1-methylpent-3-ynyloxy, 1-methylpent-4-ynyloxy, 2-methylpent-3-ynyloxy, 2-meth -methylpent-4-ynyloxy, 4-methylpent-2-ynyloxy, 1,1-dimethylbut-2-ynyloxy, 1,1- dimethylbut-3-ynyloxy, 1,2-dimethylbut-3-ynyloxy, 2,2-dimethylbut-3-ynyloxy, 1-ethylbut-2-ynyloxy, 1-ethylbut-3-ynyloxy, 2-ethylbut-3-ynyloxy or 1-ethyl-1-methylprop-2-ynyloxy, preferably 2-propynyloxy or 2-butynyloxy;

where the abovemen,tioned hydrocarbon radicals may carry from one to five halogen atoms as stated above, preferbly fluorine or, in particular, chlorine, and/or alkoxy as stated in general and in particular for R , or alkylthio as stated for $R^1$, preferably methylthio; alkylamino, such as methylamino, ethylamino, propylamino, 1-methylethylamino, butylamino, 1-methylpropylamino, 2-methylpropylamino or 1,1-dimethylethylamino;

dialkylamino, such as dimethylamino, diethylamino, dipropylamino, di-1-methylethylamino, dibutylamino, di-1-methylpropylamino, di-2-methylpropylamino, di-1,1-di-methylethylamino, ethylmethylamino, propylmethylamino, 1-methylethylmethylamino,butylmethylamino, 1-methylpropylmethylamino, 2-methylpropylmethylamino, 1,1-dimethylethylmethylamino, propylethylamino, 1-methylethylethylamino, butylethylamino, 1-methylpropylethylamino, 2-methylpropylethylamino, 1,1-dimethylethylethylamino, 1-methylethylpropylamino, butylpropylamino,1-methylpropylpropylamino, 2-methylpropylpropylamino, 1,1-dimethylethylpropylamino, 1-methylethylbutylamino, 1-methylpropylbutylamino, 2-methylpropylbutylamino or 1,1-dimethylethylbutylamino;

phenylamino;

alkylphenylamino, such as N-methyl-N-phenylamino, N-ethyl-N-phenylamino,N-phenyl-N-propylamino,N-(1-methylethyl)-N-phenylamino,N-butyl-N-phenylamino,N-(1-methyl-propyl)-N-phenylamin or N-(1,1-dimethylethyl)-N-phenylamino;

or alkylcarbonylamino, such as methylcarbonylamino, ethylcarbonylamino, propylcarbonylamino, 1-methylethylcarbonylamino, butylcarbonylamino, 1-methylpropylcarbonylamino, 2-methylpropylcarbonylamino, 1,1-dimethylethylcarbonylamino, pentylcarbonylamino, 1-methylbutylcarbonylamino, 2-methylbutylcarbonylamino, 1,1-dimethylpropylcarbonylamino, 1,2-dimethylpropylcarbonylamino, 2,2-dimethylpropylcarbonylamino, 1-ethylpropylcarbonylamino, hexylcarbonylamino, 1-methylpentylcarbonylamino,2-methylpentylcarbonylamino, 3-methylpentylcarbonylamino, 4-methylpentylcarbonylamino,1,1-dimethylbutylcarbonylamino, 1,2-dimethylbutylcarbonylamino, 1,3-dimethylbutylcarbonylamino, 2,2 TM dimethylbutylcarbonylamino,2,3-dimethylbutylcarbonylamino, 3,3-dimethylbutylcarbonylamino, 1-ethylbutylcarbonylamino, 2-ethylbutylcarbonylamino, 1,1,2-trimethylpropylcarbonylamino, 1,2,2-trimethylpropylcarbonylamino, 1-ethyl-1-methylpropylcarbonylamino or 1-ethyl-2-methylpropylcarbonylamino;

$R^4$ is hydrogen or alkyl as stated for $R^1$, preferably methyl, ethyl, propyl or 1-methylethyl;

$R^5$ is a 5-membered hetaryl, such as pyrrolyl, pyrazolyl, imidazolyl, oxadiazolyl, thiadiazolyl, oxazolyl, isoxazolyl, thiazolyl or isothiazolyl, preferably oxazolyl, isoxazolyl, oxadiazolyl, thiadiazolyl, thiazolyl or isothiazolyl, or isoxazolinyl, where these cyclic radicals may carry from one to four halogen atoms as stated for $R^3$, preferably fluorine or chlorine, and/or one or two of the following radicals:
  alkyl of 1 to 6 carbon atoms, preferably the groups stated in general for $R^1$,
  haloalkyl as stated for $R^1$, preferably trifluoromethyl; alkoxy as stated for $R^1$, preferably methoxy or ethoxy; haloalkoxy as stated in general and in particular for R:; cycloalkyl, such as cyclopropyl, cyclobutyl, cyclopentyl, cyclohexyl, cycloheptyl or cyclooctyl;
  phenyl or pyridyl, where the aromatic radicals in turn may carry from one to five halogen atoms as stated for $R^3$, preferably fluorine or chlorine, and/or from one to three of the radicals stated in general and in particular for $R^1$;

or a group $—CR^6=NOR^7$, where
  $R^6$ is hydrogen;
  alkyl as stated for $R^1$, preferably methyl, ethyl, propyl or 1-methylethyl, which may carry from one to five halogen atoms as stated for $R^3$, preferably fluorine or chlorine, and/or a phenyl ring or one of the alkoxy or alkylthio groups stated in general and in particular for $R^1$, where the phenyl ring in turn may carry from one to five halogen atoms and/or from one to three of the radicals stated in general and in particular for $R^1$;
  cycloalkyl as stated above, preferably cyclopropyl, cyclopentyl or cyclohexyl, which may carry from one to three of the alkyl groups stated in general and in particular for $R^1$;
  phenyl which may carry from one to five halogen atoms as stated for $R^3$, preferably fluorine or chlorine, and/or from one to three of the radicals stated in general and in particular for $R^1$;
  $R^7$ is alkyl of 1 to 8, preferably 1 to 4, carbon atoms, as stated for $R^1$;
  alkenyl as stated for $R^3$,
  where these radicals may carry from one to five halogen stated for $R^3$, preferably fluorine or chlorine, and/or one of the radicals stated in general and in particular for $R^1$;
  cycloalkyl as stated above, preferably cyclopropyl, cyclopentyl or cyclohexyl, which may carry from one to three of the alkyl groups stated in general and in particular for $R^1$;
  phenyl which may carry from one to five halogen atoms as stated for $R^3$, preferably fluorine or chlorine, and/or from one to three of the radicals stated in general and in particular for $R^1$;
  A is oxygen or sulfur;
  X is nitrogen or a methine group $=CR^8—$, where
    $R^8$ is one of the radicals stated in general and in particular for $R^3$,
  or $R^8$ and $R^3$ together form a 1,3-butadiene-1,4-diyl chain or an aza-1,3-diene-1,4-diyl or 2-azabuta-1,3-diene-1,4-diyl, where these chains in turn may carry from one to four halogen atoms as stated for $R^3$, preferably fluorine, chlorine or bromine, and/or one or two of the radicals stated in general and in particular for $R^1$;
  Y and Z are each nitrogen or a methine group $=CH—$, and salts thereof which can be used in agriculture.

Particularly preferred carboxylic acid derivatives of the formula I are shown in Tables A and B below.

TABLE A

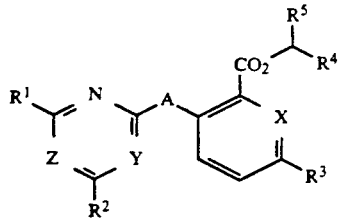

| $R^1$ | $R^2$ | Z | Y | A | X | $R^3$ | $R^4$ | $R^5$ |
|---|---|---|---|---|---|---|---|---|
| OCH$_3$ | OCH$_3$ | CH | N | O | =CF— | H | H | C(CH$_3$)=NOCH$_3$ |
| OCH$_3$ | OCH$_3$ | CH | N | O | =CF— | H | H | CH=NOCH$_2$C$_6$H$_5$ |
| OCH$_3$ | OCH$_3$ | CH | N | O | =CF— | H | H | CH=NOCH$_2$CH$_3$ |
| OCH$_3$ | OCH$_3$ | CH | N | O | =N— | H | H | C(CH$_3$)=NOCH$_2$CH$_3$ |
| OCH$_3$ | OCH$_3$ | CH | N | O | =CCl— | H | H | CH=NOCH$_2$CH=CH$_2$ |
| OCH$_3$ | OCH$_3$ | CH | N | O | =N— | H | H | CH=NOCH$_2$CH$_3$ |
| OCH$_3$ | OCH$_3$ | CH | N | O | =CCl— | H | H | C(CH$_3$)=NOCH$_2$CH$_3$ |
| OCH$_3$ | OCH$_3$ | CH | N | O | =CCl— | H | H | CH=NOCH$_2$C$_6$H$_5$ |
| OCH$_3$ | OCH$_3$ | CH | N | O | =CCl— | H | H | C(CH$_3$)=NOCH$_2$C$_6$H$_5$ |
| OCH$_3$ | OCH$_3$ | CH | N | O | =CCl— | H | H | CH=NOCH$_3$ |
| OCH$_3$ | OCH$_3$ | CH | N | O | =CCl— | H | H | CH=NOCH$_2$CH=CHCl |
| OCH$_3$ | OCH$_3$ | CH | N | O | =N— | H | H | CH=NOCH$_2$C$_6$H$_5$ |
| OCH$_3$ | OCH$_3$ | CH | N | O | =CCl— | H | H | C(CH$_3$)=NOCH$_2$CH=CH$_2$ |
| OCH$_3$ | OCH$_3$ | CH | N | O | =CCl— | H | H | 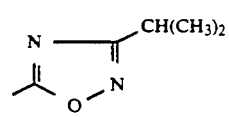 |
| OCH$_3$ | OCH$_3$ | CH | N | O | =CCl— | H | H | 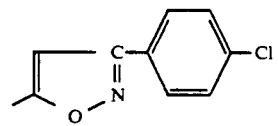 |
| OCH$_3$ | OCH$_3$ | CH | N | O | =CCl— | H | H | CH=NOCH$_2$CH$_3$ |
| OCH$_3$ | OCH$_3$ | CH | N | O | —CCl— | H | H | 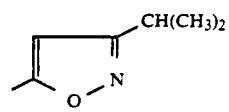 |
| OCH$_3$ | OCH$_3$ | CH | N | O | =C(CH$_3$)— | H | H | 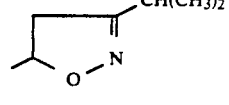 |
| OCH$_3$ | OCH$_3$ | CH | N | O | =CCl— | H | H | 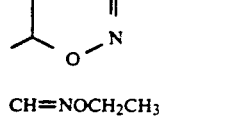 |
| OCH$_3$ | OCH$_3$ | CH | N | O | =C(OCH$_3$)— | H | H | CH=NOCH$_2$CH$_3$ |
| OCH$_3$ | OCH$_3$ | CH | N | O | =CCl— | H | CH$_3$ | CH=NOCH$_2$CH$_3$ |
| OCH$_3$ | CF$_3$ | CH | N | O | =CF— | H | H | CH=NOCH$_2$CH=CHCl |
| OCH$_3$ | OCH$_3$ | CH | N | O | =C(OCH$_2$CH=CH$_2$)— | H | H | CH=NOCH$_3$ |
| OCH$_3$ | OCH$_3$ | CH | N | S | =CCl— | H | H | CH=NOCH$_2$CH$_3$ |
| OCH$_3$ | OCH$_3$ | CH | N | S | =CCl— | H | H | C(CH$_3$)=NOCH$_2$CH$_3$ |
| OCH$_3$ | OCH$_3$ | CH | N | S | =CCl— | H | H | 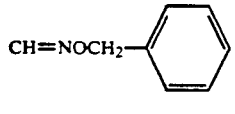 |
| OCH$_3$ | OCH$_3$ | CH | N | S | =CCl— | H | H | CH=NOCH$_2$CH=CH$_2$ |
| OCH$_3$ | OCH$_3$ | CH | N | S | =CCl— | H | H | CH=NOCH$_2$CH=CHCl |

TABLE A-continued

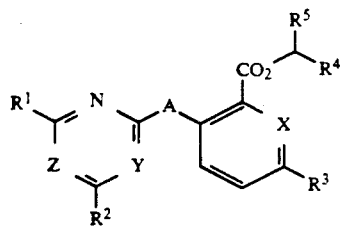

| R¹ | R² | Z | Y | A | X | R³ | R⁴ | R⁵ |
|---|---|---|---|---|---|---|---|---|
| OCH₃ | OCH₃ | CH | N | S | =CCl— | H | H | C(CH₃)=NOCH₂-phenyl |
| OCH₃ | OCH₃ | N | N | S | =CCl— | H | H | CH=NOCH₂CH₃ |
| OCH₃ | OCH₃ | N | N | O | =CCl— | H | H | CH=NOCH₂CH₃ |
| OCH₃ | OCH₃ | N | N | O | =CCl— | H | H | C(CH₃)=NOCH₂CH₃ |
| OCH₃ | OCH₃ | N | N | O | =CF— | H | H | CH=NOCH₂CH₃ |
| OCH₃ | OCH₃ | N | N | O | =CCl— | H | H | CH=NOCH₂-phenyl |
| OCH₃ | OCH₃ | N | N | O | =CCl— | H | H | CH=NOCH₂CH=CH₂ |
| OCH₃ | SCH₃ | N | N | O | =CCl— | H | H | CH=NOCH₃ |
| OCH₃ | OCH₃ | CH | N | O | =C(CF₃)— | H | H | C(CH₃)=NOCH₂-(4-Cl-phenyl) |
| OCH₃ | OCH₃ | CH | N | O | =C(OCH₂SCH₃)— | H | H | CH=NOCH₂CH=CH₂ |
| OCH₃ | OCH₃ | CH | N | O | =CCl— | H | H | CH=NOCH₂CH=CHCH₃ |
| OCH₃ | OCH₃ | CH | N | O | =CCl— | H | H | isoxazoline-cyclohexyl |
| OCH₃ | OCH₃ | CH | N | O | =CCl— | H | H | isoxazoline-(3-pyridyl) |

TABLE B

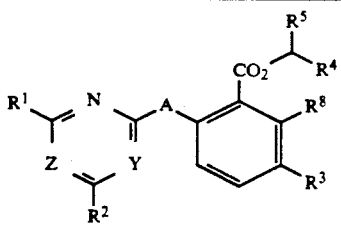

| R¹ | R² | Z | Y | A | R⁸ | R³ | R⁴ | R⁵ |
|---|---|---|---|---|---|---|---|---|
| OCH₃ | OCH₃ | CH | N | O | CH=CH—CH=CH | | H | isoxazoline-CH(CH₃)₂ |
| OCH₃ | OCH₃ | CH | N | O | CH=CH—CH=CH | | H | CH=NOCH₂CH=CHCl |
| OCH₃ | OCH₃ | CH | N | O | CH=CH—CH=CH | | H | C(CH₃)=NOCH₃ |
| OCH₃ | OCH₃ | CH | N | O | CH=CH—CH=CH | | H | CH=NOCH₂CH₃ |

TABLE B-continued

[Structure: benzene ring with substituents per formula showing R¹, R², Z, Y, A, R⁸, R³, R⁴, R⁵ positions; CO₂ group attached to CHR⁴R⁵]

| $R^1$ | $R^2$ | Z | Y | A | $R^8$ | $R^3$ | $R^4$ | $R^5$ |
|---|---|---|---|---|---|---|---|---|
| OCH₃ | OCH₃ | CH | N | O | CH=CH—CH=CH | | H | CH=NOCH₂—C₆H₅ |
| OCH₃ | OCH₃ | CH | N | O | CH=CH—CH=CH | | H | C(CH₃)=NOCH₂—C₆H₅ |
| OCH₃ | OCH₃ | CH | N | O | CH=CH—CH=CH | | H | CH=NOCH₂CH=CH₂ |
| OCH₃ | OCH₃ | CH | N | O | CH=CH—CH=CH | | H | CH=NOCH₂—C₆H₄—OCH₃ |
| OCH₃ | OCH₃ | N | N | O | CH=CH—CH=CH | | H | CH=NOCH₂CH₃ |
| OCH₃ | OCH₃ | CH | N | O | CH=CH—CBr=CH | | H | CH=NOCH₂CH₃ |
| OCH₃ | OCH₃ | CH | N | O | CF=CH—CH=CH | | H | CH=NOCH₂CH₃ |
| OCH₃ | OCH₃ | CH | N | O | CH=CH—CH=CH | | H | C(CH₃)=NOCH₂CH=CH₂ |
| OCH₃ | OCH₃ | CH | N | O | CH=CH—C(CH₃)=CH | | H | CH=NOCH₃ |

Suitable salts of the compounds of the formula I are salts which can be used in agriculture, for example alkali metal salts, such as the potassium or sodium salt, alkaline earth metal salts, such as the calcium, magnesium or barium salt, manganese, copper, zinc or iron salts and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

The novel herbicidal and growth-regulating compounds I or the agents containing them can be used, for example, in the form of directly sprayable solutions, powders, suspensions, including concentrated aqueous, oily or other suspensions or dispersions, emulsions, oil dispersions, pastes, dusts, broadcasting agents or granules, by spraying, atomizing, dusting, broadcasting or pouring. The application forms depend on the intended uses; they should in any case ensure a very fine distribution of the novel active ingredients.

Compounds I are suitable in general for the preparation of directly sprayable solutions, emulsions, pastes or oil dispersions. Suitable inert additives are mineral oil fractions of medium to high boiling point, such as kerosene or diesel oil, and coal tar oils and oils of vegetable or animal origin, aliphatic, cyclic and aromatic hydrocarbons, eg. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or highly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substrates, as such or dissolved in an oil or solvent, can be homogenized in water by means of wetting agents, adhesives, dispersants or emulsifiers. However, concentrates consisting of active substance, wetting agents, adhesives, dispersants or emulsifiers and possibly solvents or oil and suitable for dilution with water can also be prepared.

Suitable surfactants are alkali metal, alkaline earth metal and ammonium salts of aromatic sulfonic acids, for example lignin-, phenol-, naphthalene- and dibutylnaphthalenesulfonic acid, and of fatty acids, alkyl- and alkylarylsulfonates, alkyl-, laurylether- and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ethers, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, broadcasting agents and dusts can be prepared by mixing or milling together the active substances and a solid carrier.

Granules, for example, coated, impregnated and homogeneous granules, can be prepared by binding the active ingredients to solid carriers. Solid carriers are mineral earths, such as silica gel, silicas, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate, ureas and vegetable products, such as cereal meal, ground bark, woodmeal and nutshell meal, cellulose powder or other solid carriers.

The formulations contain from 0.1 to 95, preferbly from 0.5 to 90, % by weight of active ingredient. The active ingredients can be used in a purity of from 90 to 100%, preferably from 95 to 100% (according to the NMR spectrum).

The novel compounds can be formulated, for example, as follows:

I. 90 parts by weight of compound No. 1,016 are mixed with 10 parts by weight of N-methyl-α-pyrrolidone, and a solution suitable for use in the form of very small drops is obtained.

II. 20 parts by weight of compound No. 1,003 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of the calcium salt of dodecylbenzenesulfonic acid and 5 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

III. 20 parts by weight of compound No. 2,003 are dissolved in a mixture which consists of 40 parts by weight of cyclohexanone, 30 parts by weight of isobutanol, 20 parts by weight of an adduct of 7 moles of ethylene oxide with 1 mole of isooctylphenol and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

IV. 20 parts by weight of active ingredient No. 2,006 are dissolved in a mixture which consists of 25 parts by weight of cyclohexanone, 65 parts by weight of a mineral oil fraction boiling within a range from 210 to 280° C and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

V. 20 parts by weight of active ingredient No. 1,014 are thoroughly mixed with 3 parts by weight of the sodium salt of diisobutylnaphthalene-α-sulfonic acid, 17 parts by weight of the sodium salt of ligninsulfonic acid from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 1,016 are mixed with 97 parts by weight of finely divided kaolin. A dust which contains 3% by weight of the active ingredient is obtained in this manner.

VII. 30 parts by weight of active ingredient No. 1,015 are thoroughly mixed with a mixture of 92 parts by weight of silica gel powder and 8 parts by weight of liquid paraffin, which were sprayed onto the surface of the silica gel. A formulation of the active ingredient having good adhesion is obtained in this manner.

VIII. 20 parts by weight of active ingredient No. 2,004 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

The herbicides and growth regulators or the active ingredients can be applied by the preemergence or postemergence method. If the active ingredients are less well tolerated by certain crops, it is possible to use application methods in which the herbicides are sprayed with the aid of the sprayers in such a way that, as far as possible, the herbicide does not come into contact with the leaves of the sensitive crops while the active ingredients reach the leaves of undesirable plants growing underneath or the uncovered soil surface (post-directed, lay-by).

The application rates of active ingredient for use as herbicides is from 0.001 to 3, preferably from 0.01 to 1, kg/ha of active substance (a.s.), depending on the aim of control, the season, the target plants and the stage of growth.

The compounds of the formula I can influence virtually all development stages of a plant in different ways and are therefore used as growth regulators. The wide range of activity of the plant growth regulators depends in particular a) on the plant species and variety,
b) on the time of application, based on the stage of development of the plant, and on the season,
c) on the place and method of application (for example seed dressing, soil treatment, application to foliage or trunk injection in the case of trees),
d) on climatic factors, such as temperature, amount of precipitation and also length of day and light intensity,
e) on the nature of the soil (including fertilizer application),
f) on the formulation or application form of the active ingredient and finally
g) on the concentrations of active substance used.

From the number of different possible applications of the novel plant growth regulators of the formula I in plant cultivation, in agriculture and horticulture, some are mentioned below.

A. With the compounis which can be used according to the invention, it is possible greatly to inhibit the vegetative growth of the plants, which manifests itself in particular in a reduction in the growth in length. The treated plants accordingly exhibit stunted growth; furthermore, a darker leaf coloration is observed.

A practical advantage is the reduced intensity of growth of grasses at the edges of roads, in hedgerows, on canal banks and on lawn areas, such as parks, sports grounds and orchards, ornamental lawns and air fields, so that labor-intensive and expensive grass cutting can be reduced.

Increasing the strength of crops which tend to lodge, such as cereals, corn, sunflowers and soybean, is also of commercial interest. The resulting shortening and strengthening of the stem reduce or eliminate the danger of lodging of plants under unfavorable weather conditions before the harvest.

The use of growth regulators for inhibiting growth in length and for changing the time of ripening in cotton is also important. This permits completely mechanized harvesting of this important crop.

In the case of fruit trees and other trees, cutting costs can be saved using the growth regulators. Furthermore, the alternance of fruit trees can be broken by growth regulators.

By using growth regulators, it is also possible to increase or inhibit the production of side branches in plants. It is of interest to inhibit the formation of side shoots in favor of leaf growth, for example in tobacco plants.

Furthermore, growth regulators can be used to achieve a considerable increase in frost resistance, for example in winter rape. On the one hand, the growth in length and the development of leaf and plant mass which is too luxuriant (and hence particularly susceptible to frost) are inhibited. On the other hand, the young rape plants are retarded in the vegetative development stage after sowing and before the onset of the winter frosts, despite favorable growth conditions. This also eliminates the danger of frost for plants which tend to suffer a premature decline in the inhibition of blooming and to go over to the generative phase. In other crops too, for example winter cereals, it is advantageous if, as a result of treatment with novel compounds, the stocks are well tillered in the fall but start winter without excessively luxuriant growth. This makes it possible to prevent high sensitivity to frost and, because of the relatively low leaf and plant mass, attack by various diseases (for example fungal disease). The inhibition of vegetative growth also permits more dense planting of the soil in many crops, so that a greater yield can be achieved, based on the soil area.

B. With the growth regulators, it is possible to obtain higher yields of both plant parts and plant ingredients. For example, it is possible to induce the growth of greater amounts of buds, blooms, leaves, fruits, seeds, roots and tubers, to increase the content of sugar in sugar beet, sugar cane and citrus fruits, to increase the protein content in cereals or soybean or to stimulate rubber trees to produce greater latex flow.

The compounds of the formula I can increase the yield by intervening in the plant metabolism or by promoting or inhibiting vegetative and/or generative growth.

C. Finally, plant growth regulators can be used both to shorten or lengthen the development stages and to accelerate or delay ripening of the plant parts before or after harvesting.

For example, it is of commercial interest to facilitate harvesting, this being achieved by the temporarily concentrated falling or reduction in the adhesion to the tree in the case of citrus fruits, olives or other species and varieties of pomes, drupes and hard-shelled fruit. The same mechanism, ie. promotion of the formation of a-scission tissue between fruit or leaf part and shoot part of the plant is also essential for readily controllable defoliation of crops such as cotton.

D. Growth regulators can furthermore be used to reduce the water consumption of plants. This is particularly important for agricultural areas which have to be artificially irrigated at high cost, for example in arid or semiarid areas. By using the novel substances, it is possible to reduce the intensity of irrigation and hence carry out more economical farming. Growth regulators result in better utilization of the available water because, inter alia, the extent of opening of the stomata is reduced, a thicker epidermis and cuticle are formed, root penetration of the soil is improved and microclimate in the crop is advantageously affected by more compact growth.

The growth regulators of the formula I which are to be used according to the invention can be fed to the crops both via the seed (as seed dressings) and via the soil, ie. through the roots and, particularly preferably via the foliage, by spraying.

Because of the good plant toleration, the application rate can be greatly varied.

In view of the wide range of application methods, the novel compounds or the agents containing them can be used in a large number of crops for eliminating undesirable plants.

To extend the action spectrum and to achieve synergistic effects, the novel compounds I can be mixed with many members of other groups of herbicidal or growth regulating active ingredients and applied together with them. Examples of suitable components for the mixture are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ether, triazinone, uracils, benzofuran derivatives, cyclohexan-1,3-dione derivatives, quinolinecarboxylic acid derivatives, aryloxy- and hetaryloxyphenoxypropionic acids and their salts, esters and amides, etc.

It may also be advantageous to apply the compounds I alone or in combination with other herbicides, as a mixture with further crop protection agents, for example with agents for controlling pests or phytopathogenic fungi or bacteria. The miscibility with mineral salt solutions which are used for eliminating nutrient and trace element deficiencies is also of interest. Non-phytotoxic oils and oil concentrates can also be added.

Examples of synthesis

The methods described in the following examples of synthesis were used for obtaining further compounds I with appropriate modification of the starting compounds. The compounds thus obtained are listed in the Tables below with physical data.

EXAMPLE 1

Preparation of 3-isopropylisoxazol-5-ylmethyl 2-(4,6-dimethoxypyrimidin-2-yloxy)-naphthalene-1-carboxylate

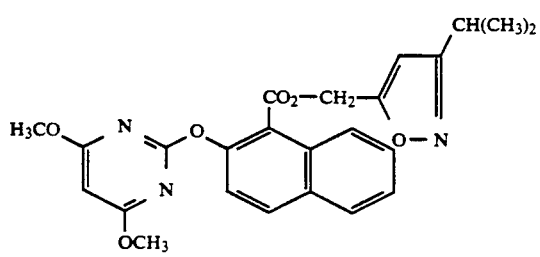

a) 2-(4,6-Dimethoxypyrimidin-2-yloxy)-naphthalene-1-carboxylic acid

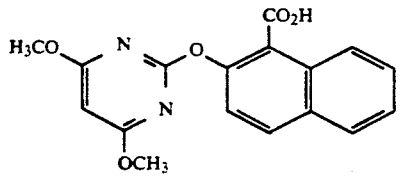

5.1 g of potassium hydroxide were added to a mixture of 14.7 g of 2-hydroxynaphthalene-1-carboxylic acid and 640 ml of methanol at 25° C. After about 10 minutes, the solvent was removed under reduced pressure. The potassium salt thus obtained was dried and then dissolved in 380 ml of dimethyl sulfoxide. 2.52 g (80% strength suspension in linseed oil) of sodium hydride were added a little at a time to this solution at 25° C. After a further 30 minutes, 17.4 g of 4,6-dimethoxy-2-methylsulfonylpyrimidine were added to the clear solution. The reaction was complete after about 12 hours. To work up the reaction mixture, water was added to it and it was freed from impurities by extraction with ethyl acetate. The acidification of the aqueous phase gave the desired product as a solid. Yield: 22 g.

b) 3-Isopropylisoxazol-5-ylmethyl 2-(4,6-dimethoxypyrimidin-5-yloxy)-naphthalene-1-carboxylate 1.7 g of potassium tert-butylate and thereafter 3.1 g of 3-isopropylisoxazol-5-ylmethyl bromide were added in succession to a mixture of 4.9 g of the naphthalenecarboxylic acid from a) and 100 ml of dimethyl sulfoxide at 25° C. After about 12 hours at 25° C., the reaction was complete. To work up the reaction mixture, it was diluted with water, acidified and extracted with ethyl acetate. The desired product was obtained in the form of an oil from the organic phase.

Yield: 3.6 g [after chromatography over silica gel]; $^1$H-NMR (250 mHz), selected signals: 1.25 (d); 3.02 (m); 3.75 (s); 5.35 (s); 5.75 (s); 6.10 (s). Active ingredient example 2,001

EXAMPLE 2

Preparation of 2-(3-chloroprop-2-en-1-yl-oximino)-ethyl 2-(4,6-dimethoxy-pyrimidin-2-yloxy)-naphthalene-1-carboxylate (E isomer)

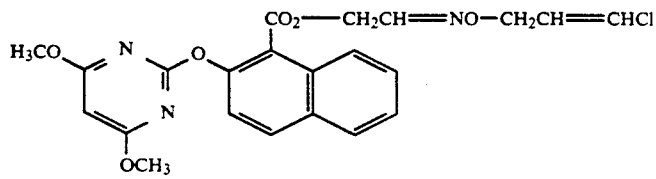

First 1.1 g of potassium tert-butylate and thereafter 1.7 g of 2-(3-chloroprop-2-en-1-yloximino)-ethyl chloride (E isomer) were added in succession to a mixture of 3.1 g of the naphthalenecarboxylic acid from 1a) and 50 ml of dimethyl sulfoxide at 25° C. After about 12 hours, the reaction was complete. To work up the reaction mixture, it was diluted with water, acidified and extracted with ethyl acetate. The desired product was obtained in the form of a solid from the organic phase.

Yield: 2.2 g [after chromatography over silica gel]; mp.: 77–83° C.

Active ingredient example 2,002

TABLE 1

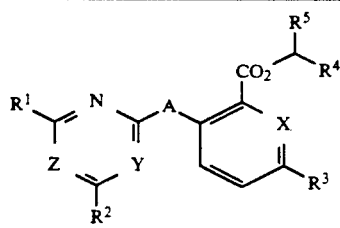

| No. | $R^1$ | $R^2$ | Z | Y | A | X | $R^3$ | $R^4$ | $R^5$ | phys. data [mp. (°C.), NMR* (δ in ppm)] |
|---|---|---|---|---|---|---|---|---|---|---|
| 1.001 | OCH$_3$ | OCH$_3$ | CH | N | O | =CF— | H | H | C(CH$_3$)=NOCH$_3$ | 71–74 |
| 1.002 | OCH$_3$ | OCH$_3$ | CH | N | O | =CF— | H | H | CH=NOCH$_2$C$_6$H$_5$ | 3,82(s), 4,73(d), 4,55(d), 5.78(s) |
| 1.003 | OCH$_3$ | OCH$_3$ | CH | N | O | =CF— | H | H | CH=NOCH$_2$CH$_3$ | 1,23(t), 3,84(s), 4,70(d), 4,92(d), 5.78(s) |
| 1.004 | OCH$_3$ | OCH$_3$ | CH | N | O | =N— | H | H | C(CH$_3$)=NOCH$_2$CH$_3$ | 74–77 |
| 1.005 | OCH$_3$ | OCH$_3$ | CH | N | O | =CCl— | H | H | CH=NOCH$_2$CH=CH$_2$ | 3,93(s), 4,80(d), 5,05(d), 5.80(s), 6.00(m) |
| 1.006 | OCH$_3$ | OCH$_3$ | CH | N | O | =N— | H | H | CH=NOCH$_2$CH$_3$ | 1,25(t), 3,80(s), 4,78(d), 5,02(d), 5,80(s) |
| 1.007 | OCH$_3$ | OCH$_3$ | CH | N | O | =N— | H | H | C(CH$_3$)=NOCH$_2$CH$_3$ | 1,23(t), 1,87(s), 3,82(s), 4,10(q), 5,80(s) |
| 1.008 | OCH$_3$ | OCH$_3$ | CH | N | O | =CCl— | H | H | CH=NOCH$_2$C$_6$H$_5$ | 3,80(s), 4,80(d), 5.07(s), 5,78(s) |
| 1.009 | OCH$_3$ | OCH$_3$ | CH | N | O | =CCl— | H | H | C(CH$_3$)=NOCH$_2$C$_6$H$_5$ | 1,90(s), 3,80(s), 4,73(s), 5,77(s) |
| 1.010 | OCH$_3$ | OCH$_3$ | CH | N | O | =CCl— | H | H | CH=NOCH$_3$ | 87–89 |
| 1.011 | OCH$_3$ | OCH$_3$ | CH | N | O | =CCl— | H | H | CH=NOCH$_2$CH=CHCl | 3,85(s), 4,80(d), 5,00(d), 5,78(s), 6,10(m) |
| 1.012 | OCH$_3$ | OCH$_3$ | CH | N | O | =N— | H | H | CH=NOCH$_2$C$_6$H$_5$ | 3,80(s), 4,80(d), 5,05(d), 5,78(d) |
| 1.013 | OCH$_3$ | OCH$_3$ | CH | N | O | =CCl— | H | H | C(CH$_3$)=NOCH$_2$CH=CH$_2$ | 1,90(s), 3,82(s), 4,57(d), 4,75(s), 5,78(d) |
| 1.014 | OCH$_3$ | OCH$_3$ | CH | N | O | =CCl— | H | H | 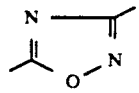 | 1,23(d), 3,78(s), 5,53(s), 6,00(s) |

TABLE 1-continued

General structure: R¹ and R² groups connected through Z=Y=N linkage to A-substituted aromatic ring bearing $CO_2CHR^4R^5$, X, and $R^3$ substituents.

| No. | R¹ | R² | Z | Y | A | X | R³ | R⁴ | R⁵ | phys. data [mp. (°C.), NMR* (δ in ppm)] |
|---|---|---|---|---|---|---|---|---|---|---|
| 1.015 | OCH₃ | OCH₃ | CH | N | O | =CCl— | H | H | (isoxazoline with C=N–4-chlorophenyl group) | 127–128 |
| 1.016 | OCH₃ | OCH₃ | CH | N | O | =CCl— | H | H | CH=NOCH₂CH₃ | 1,15(t), 3,85(s), 4,80(d), 5,05(d), 5,80(s) |
| 1.017 | OCH₃ | OCH₃ | CH | N | O | =CCl— | H | H | (isoxazoline-CH(CH₃)₂) | 1,27(d), 3,85(s), 5,27(s), 5,75(s), 6,13(s), 7,18(d) |
| 1.018 | OCH₃ | OCH₃ | CH | N | O | N | H | H | (isoxazoline-CH(CH₃)₂) | 1,25(d), 3,80(s), 5,33(s), 5,80(s), 6,20(s), 8,70(d) |

*selected signals

TABLE 2

General structure with $R^8$ and $R^3$ substituents on phenyl ring.

| No. | R¹ | R² | Z | Y | A | R⁸ | R³ | R⁴ | R⁵ | phys. data [mp. (°C.), NMR (δ in ppm)] |
|---|---|---|---|---|---|---|---|---|---|---|
| 2.001 | OCH₃ | OCH₃ | CH | N | O | CH=CH—CH=CH | | H | (isoxazoline-CH(CH₃)₂) | 1,25(d), 3,02(m), 3,75(s), 5,35(s), 5,75(s), 6,10(s) |
| 2.002 | OCH₃ | OCH₃ | CH | N | O | CH=CH—CH=CH | | H | CH=NOCH₂CH=CHCl | 77–83 |
| 2.003 | OCH₃ | OCH₃ | CH | N | O | CH=CH—CH=CH | | H | C(CH₃)=NOCH₃ | 96–98 |
| 2.004 | OCH₃ | OCH₃ | CH | N | O | CH=CH—CH=CH | | H | CH=NOCH₂CH₃ | 3,82(s), 4,87(d), 5,10(d), 5,80(s) |

Use Examples

The herbicidal action of the carboxylic acids of the formula I was demonstrated by the following greenhouse experiments:

The culture vessels used were plastic flowerpots containing loamy sand with about 3.0% of humus as a substrate. The seeds of the test plants were sown separately according to species.

In the preemergence treatment, the active ingredients emulsified or suspended in water were applied directly after sowing, by means of finely distributing nozzles. The vessels were lightly sprinkled in order to promote germination and growth and then covered with transparent plastic covers until the plants had started to grow. This covering ensures uniform germination of the test plants, unless this has been adversely affected by the active ingredients. The application rate for the preemergence use was 0.06 kg/ha of active substance.

For the postemergence treatment, the test plants were treated with the active ingredients emulsified or suspended in water, at a height of growth of from 3 to 15 cm, depending on the form of growth. The application rate of the postemergence treatment was 0.06 kg/ha of active substance.

The plants were kept at temperatures of 10–25° C. or 20–35° C., depending on the species. The test period extended over from 2 to 4 weeks. During this time, the plants were tended and their reaction to the individual treatments was evaluated.

Evaluation was based on a scale of from 0 to 100. 100 means no emergence of the plants or complete destruction of at least the above-ground parts and 0 means no damage or normal growth.

The plants used in the greenhouse experiments consisted of the following species:

| Latin name | Common name |
|---|---|
| Abutilon theophrasti | Velvet leaf |
| Amaranthus retroflexus | Redroot amaranth |
| Cassia tora | — |
| Galium aparine | Catchweed |
| Malva neglecta | Common mallow |
| Solanum nigrum | Black nightshade |

When 0.06 kg/has of active substance is used by the preemergence or postemergence method, undesirable broad-leaved plants can be very readily controlled with the example compounds 1.014, 1,015 and 1,016.

We claim:

1. A carboxylic acid derivative of the formula I

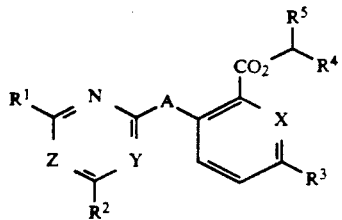

where
- $R^1$ and $R^2$ are each $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
- $R^3$ is hydrogen, hydroxyl, cyano, nitro, amino, formyl, halogen; $C_1$–$C_4$-alkyl, $C_1$–$C_4$-alkoxy, $C_3$–$C_6$-alkenyloxy, $C_3$–$C_6$-alkynyl or $C_3$–$C_6$-alkynyloxy, where these groups may carry from one to five halogen atoms and/or a $C_1$–$C_4$-alkoxy or $C_1$–$C_4$-alkylthio group; $C_1$–$C_4$-alkylamino, di-$C_1$–$C_4$-alkylamino, phenylamino, N-phenyl-N-$C_1$–$C_4$-alkylamino or $C_1$–$C_6$-alkylcarbonylamino;
- $R^4$ is hydrogen or $C_1$–$C_4$-alkyl;
- $R^5$ is a member of the group consisting of pyrrolyl, pryazolyl, imidazolyl, oxadiazolyl, thiadiazolyl, oxazolyl, isoxazolyl, thiazolyl and isothiazolyl; or is an isoxazolinyl radical, where the isoxazolinyl ring may carry from one to four halogen atoms and/or one or two of the following radicals: $C_1$–$C_6$-alkyl, $C_1$ or $C_2$-haloalkyl, $C_1$–$C_4$-alkoxy, $C_1$ or $C_2$-haloalkoxy, $C_3$–$C_8$-cycloaklyl, phenyl or pyridyl, where the aromatic radicals in turn may carry from one to five halogen atoms and/or from one to three of the radicals stated for $R^1$;
or a group —$CR^6$=$NOR^7$, where
- $R^6$ is hydrogen; $C_1$–$C_4$-alkyl which may carry from one to five halogen atoms and/or one of the following radicals: $C_1$–$C_4$-alkoxyl, $C_1$–$C_4$-alkylthio or phenyl, where the phenyl radical in turn may carry from one to five halogen atoms and/or from one to three of the radicals stated for $R^1$, or $R^6$ is $C_3$–$C_8$-cycloalkyl which may carry from one to three $C_1$–$C_4$-alkyl groups, or $R^6$ is phenyl which may carry from one to five halogen atoms and/or from one to three of the radicals stated for $R^1$, and
- $R^7$ is $C_1$–$C_8$-alkyl or $C_3$–$C_6$-alkenyl which may carry fron one to five halogen atoms and/or one of the following radicals: $C_1$–$C_4$-alkoxy, $C_1$–$C_4$-alkylthio or phenyl, where the phenyl radical in turn may carry from one to five halogen atoms and/or from one to three of the radicals stated for $R^1$;
- $C_3$–$C_8$-cycloalkyl which may carry from one to three $C_1$–$C_4$-alkyl groups;
- phenyl which may carry from one to five halogen atoms and/or from one to three of the radicals stated for $R^1$;
- A is oxygen or sulfur;
- X is nitrogen or a methine group =$CR^8$— where $R^8$ is one of the radicals $R^3$, or $R^8$ and $R^3$ together form a member of the group consisting of 1-azabuta-1,3-diene-1,4-diyl and 2-azabuta-1,3-diene-1,4-diyl;
- Y is N and Z is CH, or
- Y is CH and Z is N, and its salts which can be used in agriculture.

2. A carboxylic acid derivative I as defined in claim 1, wherein $R^1$ and $R^2$ are each methoxy, $R^3$ and $R^4$ are each H, $R^5$ is 3- isopropylisoxazol-5-ylmethyl, X is=CCl, Y is N, Z is CH and A is 0.

3. A method for controlling undesirable plant growth, wherein the undesirable plants and/or their habitat are treated with a herbicidally effective amount of a derivative I as defined in claim 2.

4. A herbicidal composition containing a herbicidally effective amount of a compound as claimed in claim 1 and inert additives.

5. A method for controll undesirable plant growth, wherein the undesirable plants and/or their habitat are treated with a herbicidally effective amount of a derivative I as defined in claim 1.

6. A plant growth regulator composition containing a plant growth regulating effective amount of a compound as claimed in claim 1 and inert additives.

7. A method for regulating plant growth, wherein an amount, having a regulating effect, of a compound of the formula I as defined in claim 1 is allowed to act on the seeds, the plant and/or their habitat.

* * * * *

UNITED STATES PATENT AND TRADEMARK OFFICE
CERTIFICATE OF CORRECTION

PATENT NO. : 5,085,685
DATED : Feb. 4, 1992
INVENTOR(S) : RHEINHEIMER et al.

It is certified that error appears in the above-identified patent and that said Letters Patent is hereby corrected as shown below:

Claim 1, column 21, line 37, between "," and "$C_3$-$C_6$-" insert --$C_3$-$C_6$-alkenyl,--.

Signed and Sealed this

Twenty-fifth Day of May, 1993

Attest:

MICHAEL K. KIRK

Attesting Officer     Acting Commissioner of Patents and Trademarks